(12) United States Patent
Sudol et al.

(10) Patent No.: US 11,504,091 B2
(45) Date of Patent: Nov. 22, 2022

(54) TRANSDUCER ARRAYS WITH AIR KERFS FOR INTRALUMINAL IMAGING

(71) Applicant: KONINKLIJKE PHILIPS N.V., Eindhoven (NL)

(72) Inventors: Wojtek Sudol, Andover, MA (US); Anjali Saini, Sudbury, MA (US); Junho Song, North Andover, MA (US); Hyunggyun Lee, Woburn, MA (US); Mike Lavy, Stoneham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 685 days.

(21) Appl. No.: 16/338,788

(22) PCT Filed: Oct. 3, 2017

(86) PCT No.: PCT/EP2017/075057
§ 371 (c)(1),
(2) Date: Apr. 2, 2019

(87) PCT Pub. No.: WO2018/065405
PCT Pub. Date: Apr. 12, 2018

(65) Prior Publication Data
US 2021/0275142 A1    Sep. 9, 2021

Related U.S. Application Data

(60) Provisional application No. 62/434,568, filed on Dec. 15, 2016, provisional application No. 62/403,267, filed on Oct. 3, 2016.

(51) Int. Cl.
*A61B 8/00* (2006.01)
*A61B 8/12* (2006.01)
*B06B 1/06* (2006.01)
*H01L 41/311* (2013.01)
*H01L 41/293* (2013.01)

(52) U.S. Cl.
CPC .............. *A61B 8/4488* (2013.01); *A61B 8/12* (2013.01); *A61B 8/445* (2013.01); *B06B 1/0622* (2013.01); *H01L 41/293* (2013.01); *H01L 41/311* (2013.01)

(58) Field of Classification Search
CPC ......... A61B 8/12; A61B 8/445; A61B 8/4488; B06B 1/0622; H01L 41/293; H01L 41/311
USPC ....................................................... 310/311
See application file for complete search history.

(56) References Cited

U.S. PATENT DOCUMENTS

| | | |
|---|---|---|
| 4,217,516 A | 8/1980 | Iinuma et al. |
| 4,890,268 A | 12/1989 | Smith et al. |
| 5,320,104 A | 6/1994 | Fearnside et al. |
| 5,671,746 A | 9/1997 | Dreschel et al. |
| 6,278,224 B1 | 8/2001 | Sawada et al. |
| 6,390,985 B1 | 5/2002 | Mamayek |
| 2015/0141833 A1* | 5/2015 | Dayton ............... A61B 8/4477 600/463 |

(Continued)

*Primary Examiner* — Emily P Pham
*Assistant Examiner* — Monica Mata

(57) ABSTRACT

An imaging assembly for an intraluminal device is provided. In one embodiment, the imaging assembly includes: an array of ultrasound transducer elements spaced apart by air kerfs; a plurality of buffer elements surrounding the array of ultrasound transducer elements, wherein the plurality of buffer elements are spaced apart by gaps; and a sealing material filling portions of the gaps between the plurality of buffer elements.

8 Claims, 12 Drawing Sheets

(56) References Cited

U.S. PATENT DOCUMENTS

2015/0305708 A1   10/2015   Stigall et al.

* cited by examiner

TRANSDUCER ARRAYS WITH AIR KERFS FOR INTRALUMINAL IMAGING

RELATED APPLICATIONS

This application is the U.S. National Phase application under U.S.C. 0 371 of International Application No. PCT/EP2017/075057, filed on Oct. 3, 2017, which claims the benefit of and priority to U.S. Provisional Application Nos. 62/403,267, filed Oct. 3, 2016, and 62/434,568, filed Dec. 15, 2016, which are incorporated by reference in their entireties.

TECHNICAL FIELD

The present disclosure relates generally to intraluminal imaging and, in particular, to techniques for fabricating imaging components including a transducer array with air kerfs.

BACKGROUND

Minimally invasive surgeries have been enabled by the advance of various medical technologies. For example, diagnostic and therapeutic ultrasound catheters have been designed for imaging inside areas of the human body. In the cardiovascular system, two common diagnostic ultrasound methods are intravascular ultrasound (IVUS) and intra-cardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image chambers of the heart and surrounding structures, for example, to guide and facilitate medical procedures, such as transseptal lumen punctures, left atrial appendage closures, atrial fibrillation ablation, and valve repairs. Commercially-available ICE catheters are not designed to be delivered over a guidewire, but instead have distal ends which can be articulated by a steering mechanism located in a handle at the proximal end of the catheter. For example, an ICE catheter may be inserted through the femoral or jugular artery when accessing the anatomy, and steered in the heart to acquire images necessary to the safety of the medical procedures.

An ICE catheter typically includes an ultrasound imaging component that generates and receives acoustic energy. The imaging core may include a lined array of transducer elements or transducer elements arranged in any suitable configuration. The imaging component is encased in a tip assembly located at a furthest distal tip of the catheter. The tip assembly is covered with acoustic adhesive materials. An electrical cable is connected to the imaging component and extends through the core of the body of the catheter. The electrical cable may carry control signals and echo signals to facilitate imaging of the heart anatomy. The device may provide rotational, 2-way, or 4-way steering mechanisms such that anterior, posterior, left, and/or right views of the heart anatomy may be imaged.

An imaging component typically includes an array of ultrasound transducer elements, where the spaces between the individual ultrasound transducer elements are filled with a filler material such as a polymer or an epoxy material. The spaces are referred to as kerfs. However, imaging components with air kerfs or non-filled kerfs are known to provide a higher performance (e.g., directivity, bandwidths, and output pressures) than imaging components with filled kerfs since the air kerfs allow individual ultrasound transducer elements to function independent of each other.

The manufacturing of imaging components with air kerfs is challenging. For example, the imaging component is typically encased in a housing filled with an encapsulating material. The encapsulating material can easily infiltrate into the air kerfs between the ultrasound transducer elements causing the air kerfs to be completed filled or partially filled instead of non-filled. One approach to protecting the air kerfs is to wrap all surfaces or sides of the array with a sealing film. However, the sealing film increases the footprint of the imaging component, which may not be desirable since catheters are space-limited. In addition, the wrapping of the ground plane may not completely seal the sides or surfaces of the array structure from infiltration of cleaning fluids, epoxies, or window material that are applied in subsequent fabrication process steps.

SUMMARY

The invention provides devices, systems, and related methods for manufacturing imaging components with air kerfs that overcome the limitations associated with previous designs.

Embodiments of the present disclosure provide an imaging component with air kerfs between ultrasound transducer elements. The imaging component includes an array structure including ultrasound transducer elements and buffer elements. The ultrasound transducer elements are arranged in rows and columns spaced apart by air kerfs. The buffer elements are positioned at the outer-most rows and the outer-most columns of the array structure forming a border or buffering region in the array structure. A sealing material is applied around the sides or circumferences of the array structure. The sealing material is allowed to wick into at least some portions of the gaps between the buffer elements. The sealing material prevents other material and/or fluid in subsequent fabrication procedures from spreading into the air kerfs. The disclosed embodiments are compatible with catheter manufacturing processes. The sealing material allows the air kerfs to remain unfilled without increasing the footprint of the imaging component. The disclosed embodiments can be applied to fabricate ultrasound transducer arrays including any number of rows and any number of columns for any catheter imaging including ICE and IVUS imaging.

In one embodiment, an imaging assembly for an intraluminal device is provided. The imaging assembly includes: an array of ultrasound transducer elements spaced apart by air kerfs; a plurality of buffer elements surrounding the array of ultrasound transducer elements, wherein the plurality of buffer elements are spaced apart by gaps; and a sealing material filling portions of the gaps between the plurality of buffer elements.

In some embodiments, the air kerfs separate adjacent ultrasound transducer elements of the array of ultrasound transducer elements by a distance of 30 micrometers (μm) or less. In some embodiments, the gaps between the plurality of buffer elements are aligned to the air kerfs. In some embodiments, the sealing material fills the portions of the gaps to a depth of at least 20 micrometers (μm) from an outer boundary of the plurality of buffer elements. In some embodiments, the sealing material includes an ultraviolet (UV) epoxy material. In some embodiments, the imaging assembly further includes a ground edge plating to provide a ground return for the array of ultrasound transducer elements; and a ground plane connecting the array of ultrasound transducer elements and the plurality of buffer elements to the ground edge plating. In some embodiments, the imaging assembly further includes an integrated circuit (IC) layer, wherein the array of ultrasound transducer elements is positioned adjacent a top plane of the IC layer; and a backing layer positioned adjacent a bottom plane of the IC layer. In some embodiments, the imaging assembly further includes an encapsulating material securing the imaging assembly within the intraluminal device, wherein the sealing material prevents the encapsulating material from reaching the air kerfs.

In one embodiment, a method of manufacturing an imaging assembly is provided. The method includes forming an array of ultrasound transducer elements spaced apart by air kerfs; forming a plurality of buffer elements surrounding the array of ultrasound transducer elements, wherein the plurality of buffer elements are spaced apart by gaps; filling at least a portion of the gaps between the plurality of buffer elements with a sealing material; and curing the sealing material filling at least the portion of the gaps between the plurality of buffer elements such that the array of ultrasound transducer elements remain spaced apart by the air kerfs.

In some embodiments, the air kerfs separate adjacent ultrasound transducer elements of the array of transducer elements by a distance of 30 micrometers (µm) or less. In some embodiments, the gaps separate adjacent buffer elements by a distance of 30 micrometers (µm) or less. In some embodiments, the sealing material includes an ultraviolet (UV) epoxy material. In some embodiments, the filling at least the portion of the gaps between the plurality of buffer elements includes wicking the sealing material into the gaps. In some embodiments, the curing the sealing material filling at least the portion of the gaps between the plurality of buffer elements includes applying an UV activating light to the sealing material before the sealing material reaches the air kerfs. In some embodiments, the method further includes coupling the array of ultrasound transducer elements to a ground edge plating, wherein the ground edge plating provides an electrical ground return for the array of ultrasound transducer elements. In some embodiments, the coupling the array of ultrasound transducer elements to the ground edge plating includes coupling a ground plane to the array of ultrasound transducer elements and the ground edge plating. In some embodiments, the array of ultrasound transducer elements and the plurality of buffer elements are formed as part of an imaging component that includes an integrated circuit (IC) layer and a backing material layer. In some embodiments, the method further includes positioning the imaging component within a tip member; and securing the imaging component within the tip member with an encapsulating material, wherein the cured sealing material prevents the encapsulating material from reaching the air kerfs. In some embodiments, the method further includes coupling the tip member with the imaging component secured therein to a distal portion of an intraluminal device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
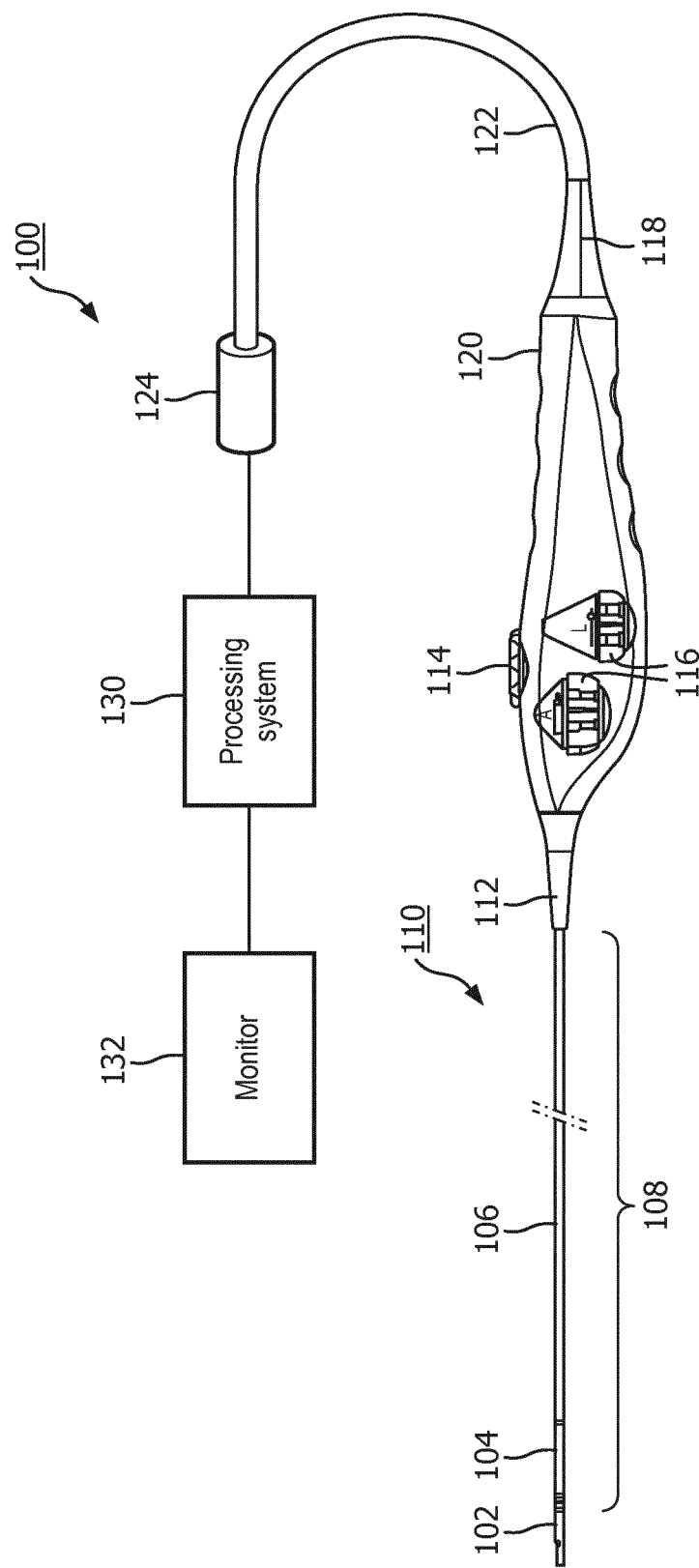
FIG. 1 is a schematic diagram of an intraluminal imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intraluminal system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100 according to embodiments of the present disclosure. The system 100 may include an intraluminal device 110, a connector 124, a control and processing system 130, such as a console and/or a computer, and a monitor 132. The intraluminal device 110 includes a tip assembly 102, a flexible elongate member 108, and a handle 120. The flexible elongate member 108 includes a distal portion 104 and a proximal portion 106. The distal end of the distal portion 104 is attached to the tip assembly 102. The proximal end of the proximal portion 106 is attached to the handle 120 for example, by a resilient strain reliever 112, for manipulation of the intraluminal device 110 and manual control of the intraluminal device 110. The tip assembly 102 can include an imaging component with ultrasound transducer elements and associated circuitry. The handle 120 can include actuators 116, a clutch 114, and other steering control components for steering the intraluminal device 110. In an embodiment, the intraluminal device 110 is an ICE device.

The handle 120 is connected to the connector 124 via another strain reliever 118 and an electrical cable 122. The connector 124 may be configured in any suitable configurations to interconnect with the processing system 130 and the monitor 132 for processing, storing, analyzing, manipulating, and displaying data obtained from signals generated by the imaging core at the tip assembly 102. The processing system 130 can include one or more processors, memory, one or more input devices, such as keyboards and any suitable command control interface device. The processing system 130 can be operable to facilitate the features of the intraluminal imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the tip assembly 102 and the distal portion 104 in a left-right plane and the other actuator 116 may deflect the tip assembly 102 and the distal portion 104 in an anterior-posterior plane. The clutch 114 provides a locking mechanism to lock the positions of the actuators 116 and in turn the deflection of the flexible elongate member 108 while imaging the area of interest.

The imaging process may include activating the ultrasound transducer elements on the tip assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the repletion of the echo signals. In some embodiments, the processing system 130 and the monitor 132 may be part of the same system.

The system 100 may be utilized in a variety of applications such as transseptal lumen punctures, left atrial appendage closures, atrial fibrillation ablation, and valve repairs and can be used to image vessels and structures within a living body. In addition, the tip assembly 102 may include any suitable physiological sensor or component for diagnostic, treatment, and/or therapy. For example, the tip assembly can include an imaging component, an ablation component, a cutting component, a morcellation component, a pressure-sensing component, a flow-sensing component, a temperature-sensing component, and/or combinations thereof.

Figure 2:
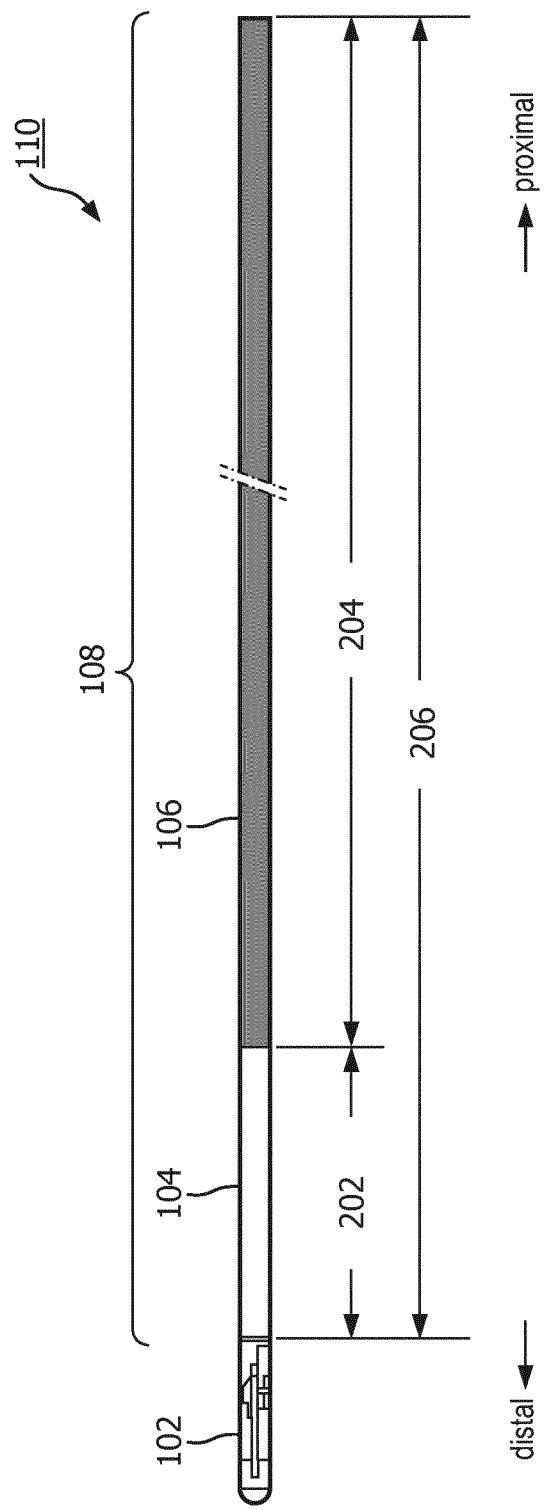
FIG. 2 is a schematic diagram of a portion of an intraluminal device according to embodiments of the present disclosure.

FIG. 2 is a schematic diagram of a portion of the intraluminal device 110 according to embodiments of the present disclosure. The tip assembly 102 and the flexible elongate member 108 are shaped and sized for insertion into vessels of a patient body. The flexible elongate member 108 can be composed of any suitable material, such as Pebax® polyether block amides. The distal portion 104 and the proximal portion 106 are tubular in shape and may include one or more lumens extending along a length of the flexible elongate member 108. In some embodiments, one lumen (e.g., a primary lumen) may be sized and shaped to accommodate an electrical cable 340 (shown in FIG. 3) interconnecting the tip assembly 102 and the connector 124 for transferring echo signals obtained from the transducer elements. In addition, the lumen may be shaped and sized to accommodate other components for diagnostic and/or therapy procedures. In some other embodiments, one or more lumens (e.g., secondary lumens) may be sized and shaped to accommodate steering wires, for example, extending from the distal portion 104 to the handle 120. The steering wires may be coupled to the actuators 116 and the clutch 114 such that the flexible elongate member 108 and the tip assembly 102 are deflectable based on actuations of the actuators 116 and the clutch 114. Dimensions of the flexible elongate member 108 can vary in different embodiments. In some embodiments, the flexible elongate member 108 can be a catheter having an outer diameter between about 8 and about 12 French (Fr) and can have a total length 206 between about 80 centimeters (cm) to about 120 cm, where the proximal portion 106 can have a length 204 between about 70 cm to about 118 cm and the distal portion 104 can have a length 202 between about 2 cm to about 10 cm.

Figure 3:
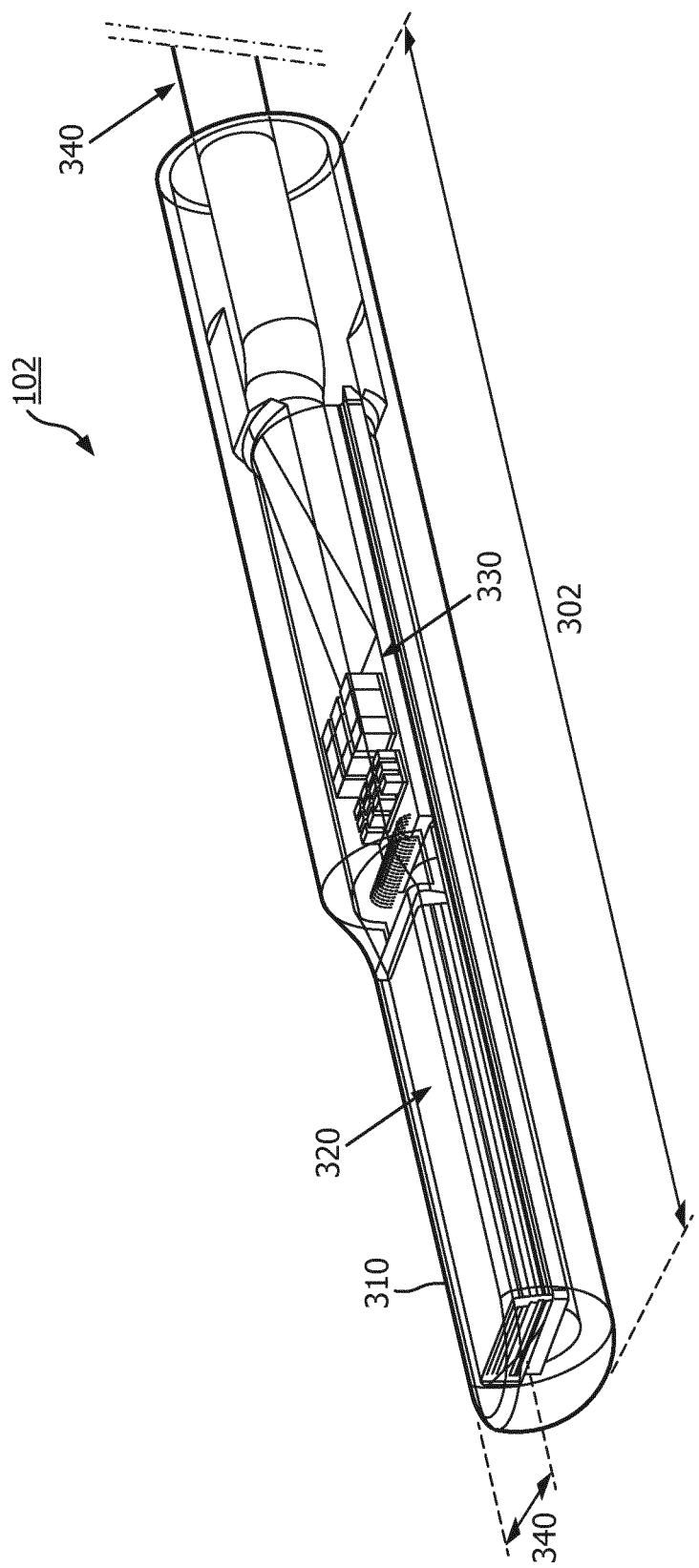
FIG. 3 is a schematic diagram of a tip assembly according to embodiments of the present disclosure.

FIG. 3 is a schematic diagram of the tip assembly 102 according to embodiments of the present disclosure. FIG. 3 provides a more detailed view of the tip assembly 102. The tip assembly 102 includes a tip member 310, an imaging component 320, and an interposer 330. The tip member 310 has a tubular body sized and shaped for insertion into a patient body. The tip member 310 can be composed of a thermoplastic elastomer material or any suitable biocompatible material that has acoustic impedance matching to blood within a vessel of a patient body when in use. For example, the tip member 310 can be composed of Pebax® polyether block amides. Dimensions of the tip member 310 can vary in different embodiments and may depend on the size of the catheter or the flexible elongate member 108. In some embodiments, the tip member 310 can include a length 302 between about 15 millimeter (mm) to about 30 mm and a width 304 between about 2 mm to about 4 mm.

The interposer 330 interconnects the imaging component 320 to an electrical cable 340. The imaging component 320 emits ultrasound energy and receives ultrasound echo signals reflected by surrounding tissues and vasculatures. The imaging component 320 is described in greater detail herein with references to FIG. 4. The electrical cable 340 extends along a length of the flexible elongate member 108 and may be coupled to the cable 122. The electrical cable 340 carries the ultrasound echo signals to the processing system 130 for image generation and analysis. In addition, the electrical cable 340 can carry control signals for controlling the imaging component 320. Further, the electrical cable 340 can carry power for powering the imaging component 320.

Figure 4A:
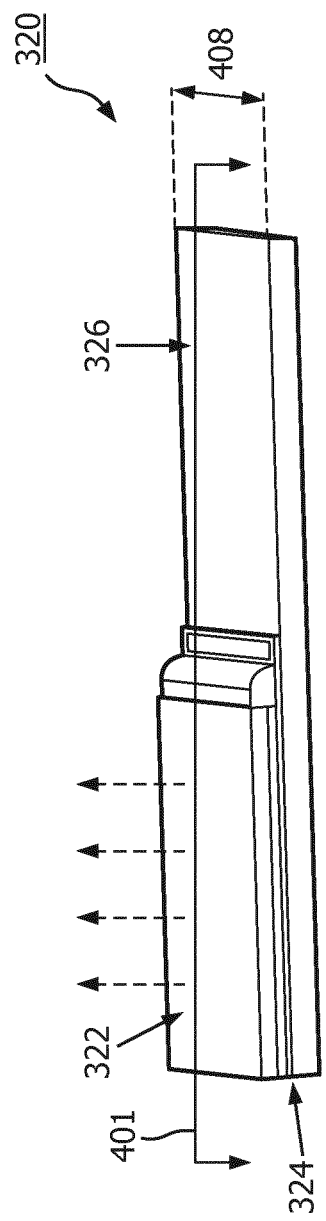
FIG. 4A is a perspective view of an imaging component according to embodiments of the present disclosure.
Figure 4B:
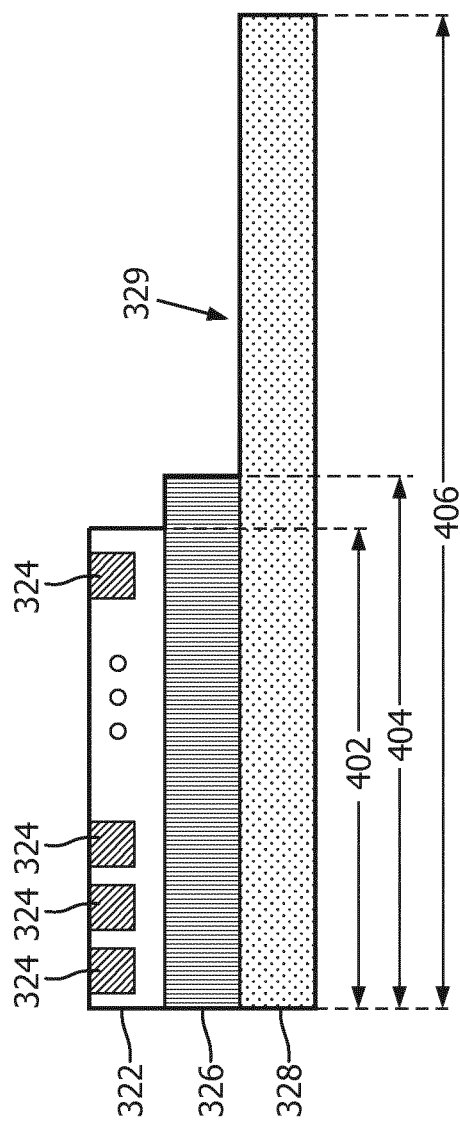
FIG. 4B is a cross-sectional view of an imaging component according to embodiments of the present disclosure.

FIG. 4A is a perspective view of the imaging component 320 according to embodiments of the present disclosure. FIG. 4B is a cross-sectional view of the imaging component 320 take along the line 401 of FIG. 4A according to embodiments of the present disclosure. The imaging component 320 is a planar component including an acoustic layer 322, an integrated circuit (IC) layer 326, and a backing layer 328. The IC layer 326 is positioned between the acoustic layer 322 and the backing layer 328.

The acoustic layer 322 includes an array of ultrasound transducer elements 324. The ultrasound transducer elements 324 are composed of piezoelectric material. Exemplary transducers for ICE have a typical thickness of approximately 0.28 mm in the piezoelectric material to enable an 8 megahertz (MHz) ultrasound signal to be generated and transmitted at a typical velocity of 1500 meter per second (m/sec) through blood. The ultrasound signal may propagate in the direction as shown by the dashed arrows. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by a driving voltage on the transducers. In some embodiments, the acoustic layer 322 may include a linear array of about 32 to about 128 ultrasound transducer elements 324 for two-dimensional (2D) imaging. In some other embodiments, the acoustic layer 322 may include a matrix of about 200 to about 900 ultrasound transducer elements 324 for three-dimensional (3D) imaging.

The IC layer 326 includes integrated logics and/or circuitries formed from a semiconductor material, such as silicon. The integrated logics and/or circuitries are configured to multiplex control signals, for example, generated by the processing system 130, and transfer the control signals to corresponding ultrasound transducer elements 324. The controls signals can control the emission of ultrasound pulses and/or the reception of echo signals. In the reverse direction, the integrated logics and/or circuitries are configured to receive ultrasound echo signals reflected by target tissue and received by the ultrasound transducer elements 324. The integrated logics and/or circuitries convert the ultrasound echo signals into electrical signals and transfer the electrical signals through the interposer 330 and the electrical cable 340 to the processing system 130 for processing and/or display. The integrated logics and/or circuitries can be further configured to perform signal conditioning before transferring the signals. Signal conditioning may include filtering, amplification, and beamforming. In some embodiments, the IC layer 326 may have a longer length than the acoustic layer 322 for coupling to the interposer 330.

The backing layer 328 is composed of an acoustically absorptive material so that the backing layer 328 can absorb or deaden the ultrasonic waves coming from the back of the acoustic layer 322. For example, the backing layer 328 may be composed of a polymeric material. In some embodiments, the backing layer 328 can have a longer length than IC layer 326. The portion 329 of the backing layer 328 extending beyond the IC layer 326 may function as an alignment agent, where the interposer 330 is positioned on top of the portion 329 when coupled to the IC layer 326.

Dimensions of the imaging component 320 may vary in different embodiments and may be limited by the space available in the tip member 310. For example, the acoustic layer 322, the IC layer 326, and the backing layer 328 may have about the same width 408, which may be in the range of about 1.6 mm to about 4 mm. The acoustic layer 322 may have a length 402 of about 7 mm to about 15 mm. The IC layer 326 may have a length 404 of about 8 mm to about 17 mm. The backing layer 328 may have a length 406 of about 10 mm to about 20 mm.

Figure 5:
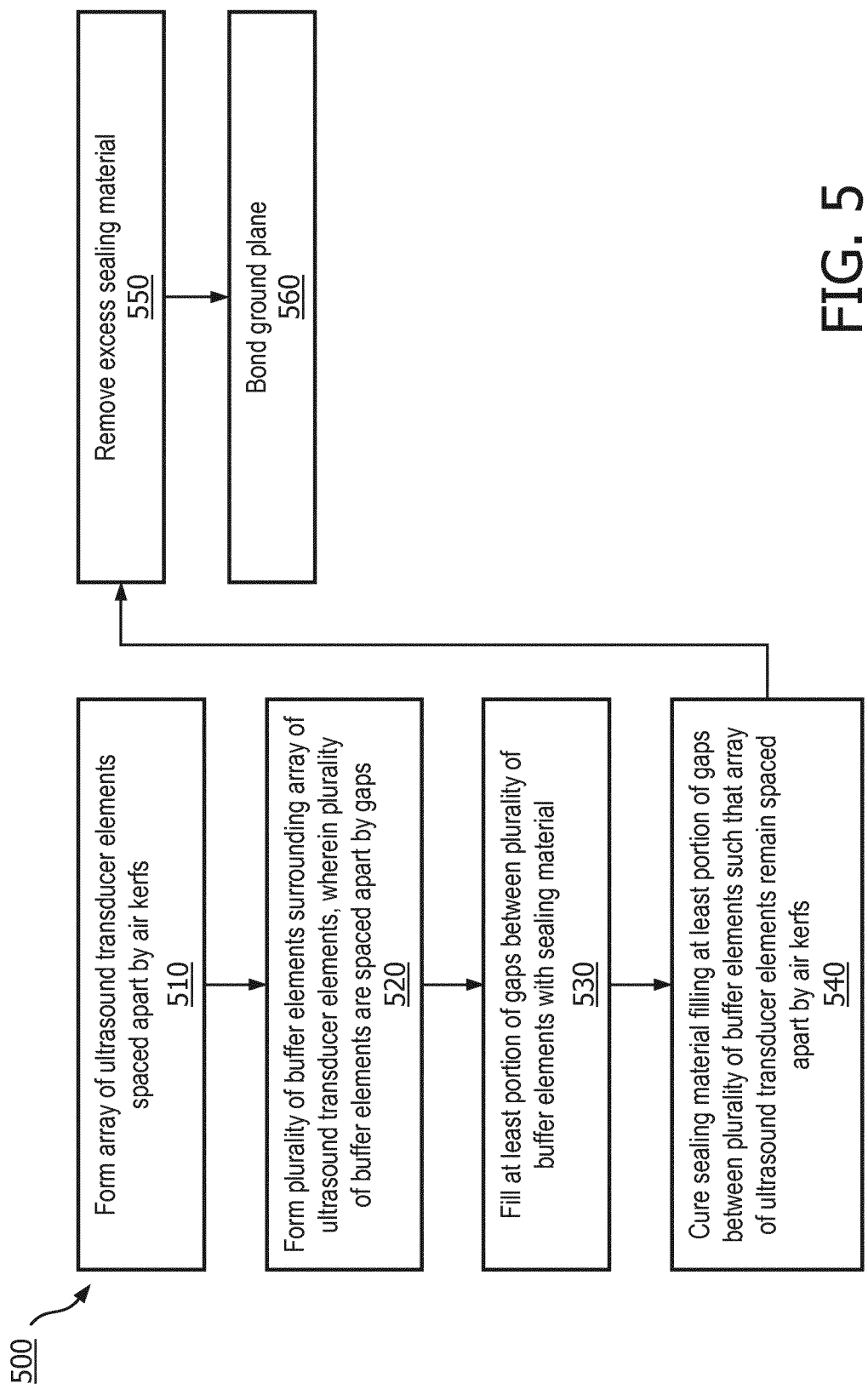
FIG. 5 is a flow diagram of a method of manufacturing an imaging component according to embodiments of the present disclosure.
Figure 6:
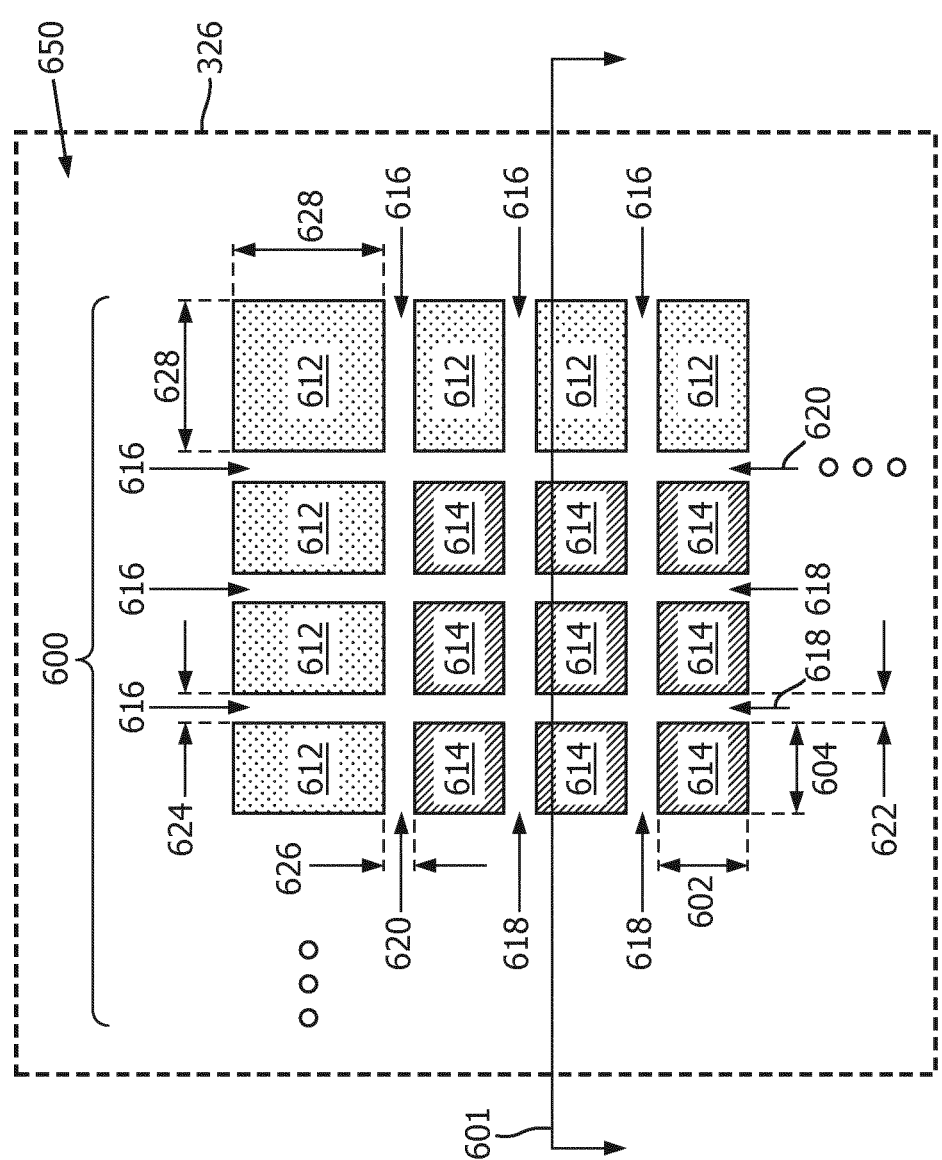
FIG. 6 is a top view of an array structure coupled to an integrated circuit (IC) layer in a stage of manufacturing according to embodiments of the present disclosure.
Figure 7:
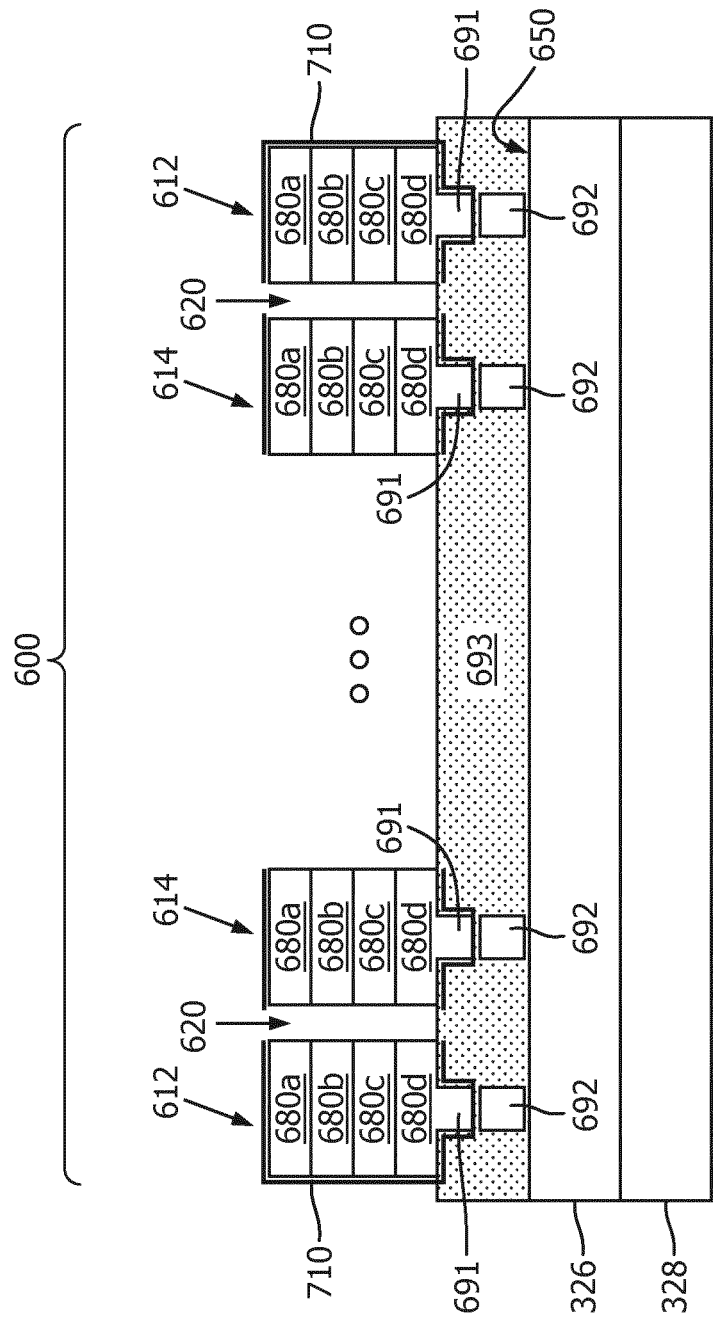
FIG. 7 is a cross-sectional view of an array structure coupled to an IC layer in a stage of manufacturing according to embodiments of the present disclosure.
Figure 8:
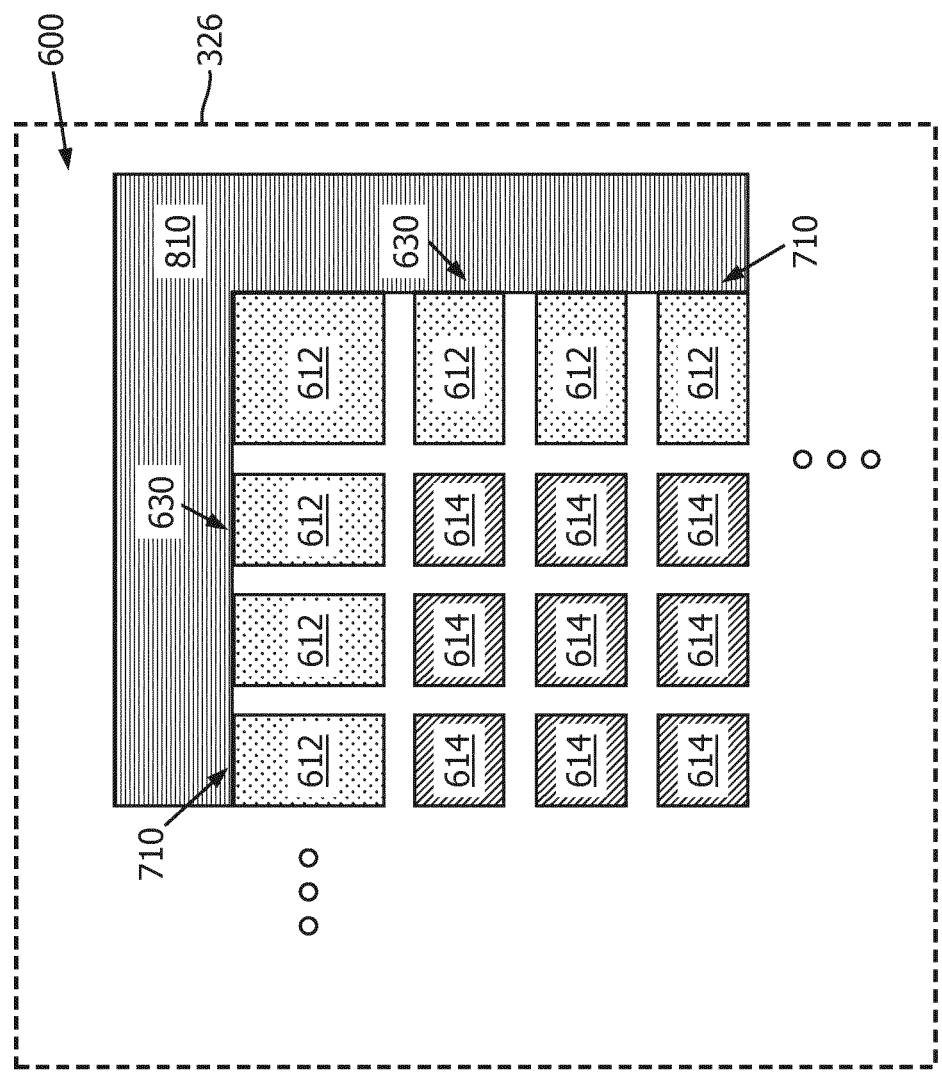
FIG. 8 is a top view of an array structure sealed with a sealing material in a stage of manufacturing according to embodiments of the present disclosure.
Figure 9:
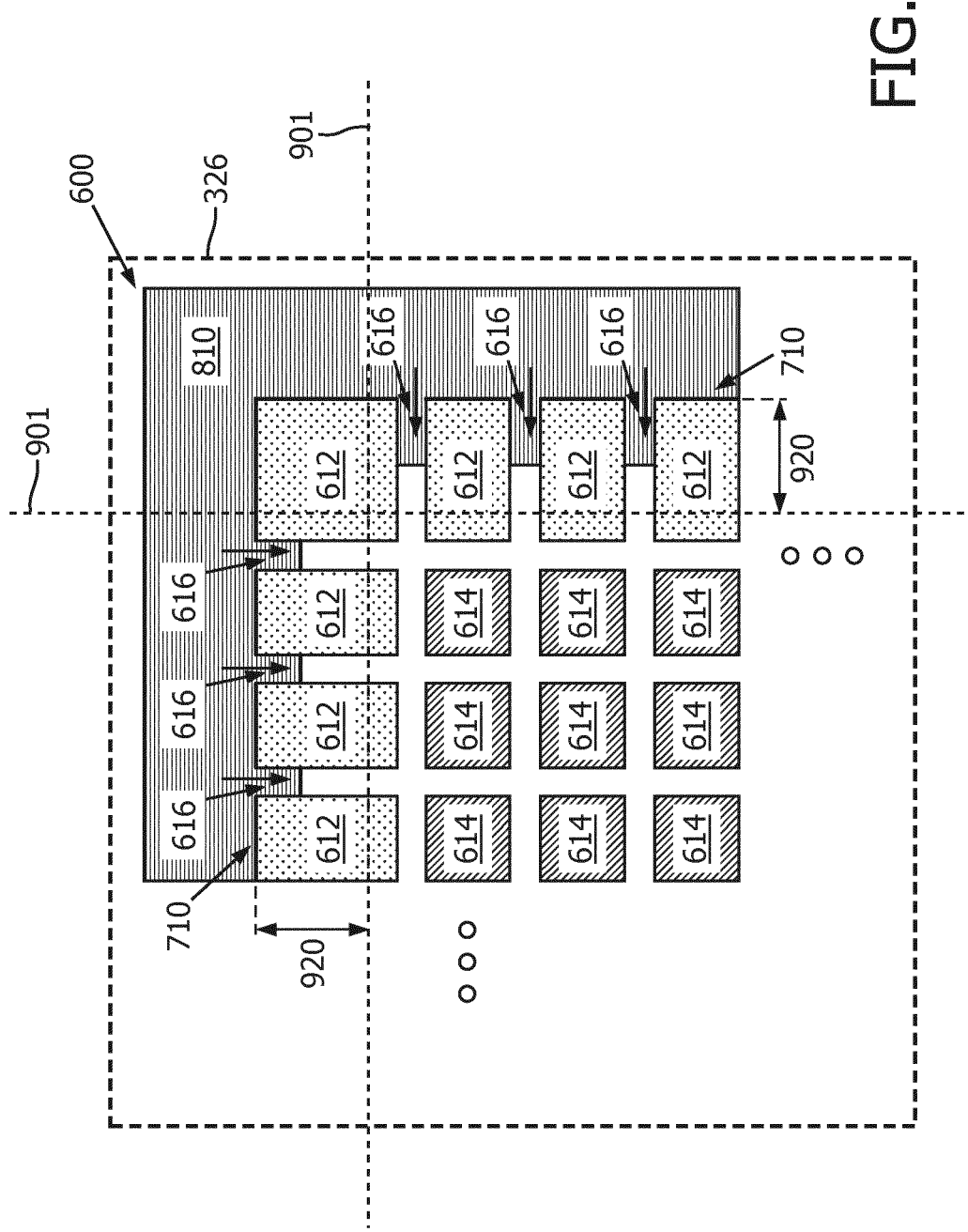
FIG. 9 is a top view of an array structure under a wicking process in a stage of manufacturing according to embodiments of the present disclosure.
Figure 10:
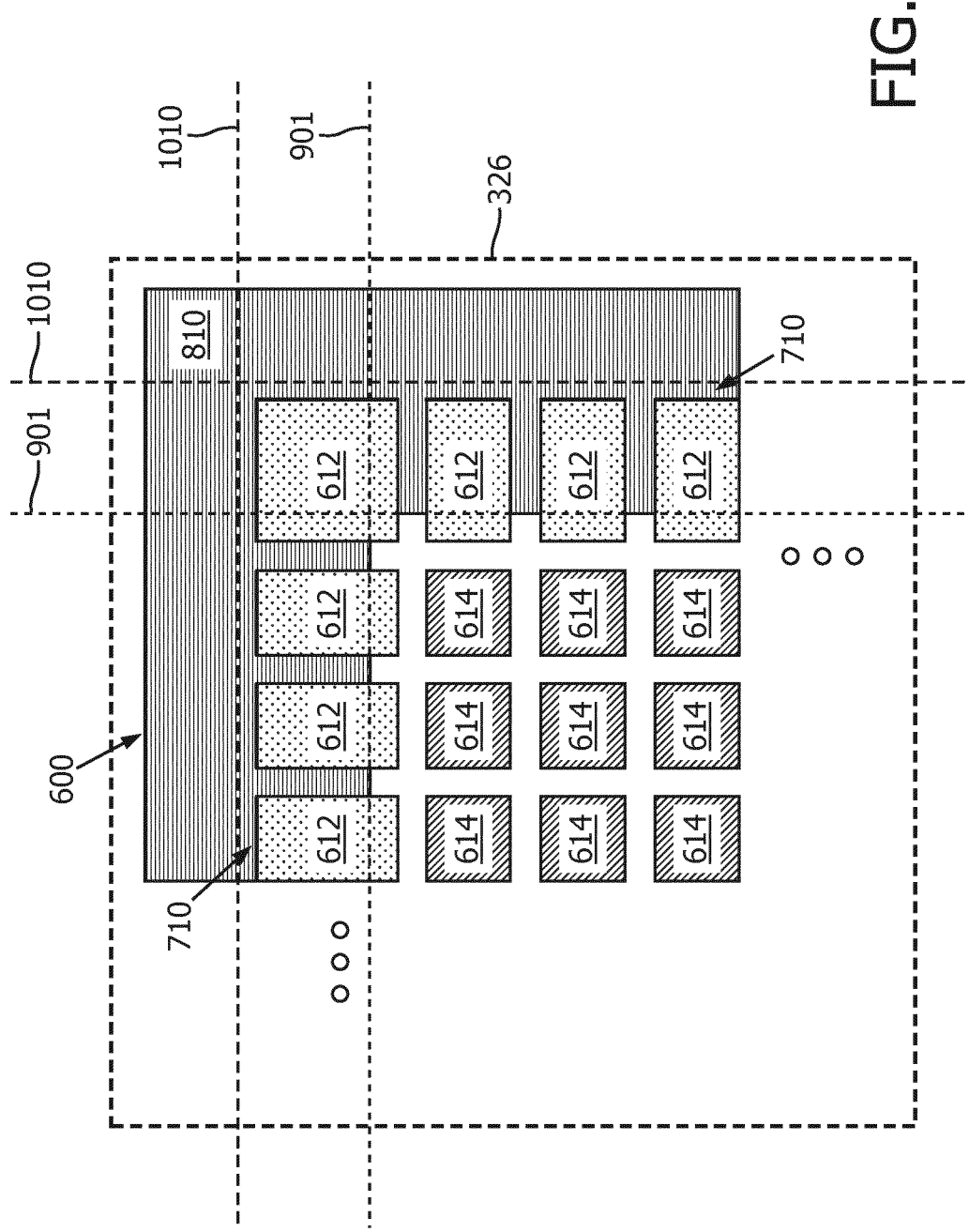
FIG. 10 is a top view of an array structure after a wicking process is completed in a stage of manufacturing according to embodiments of the present disclosure.
Figure 11:
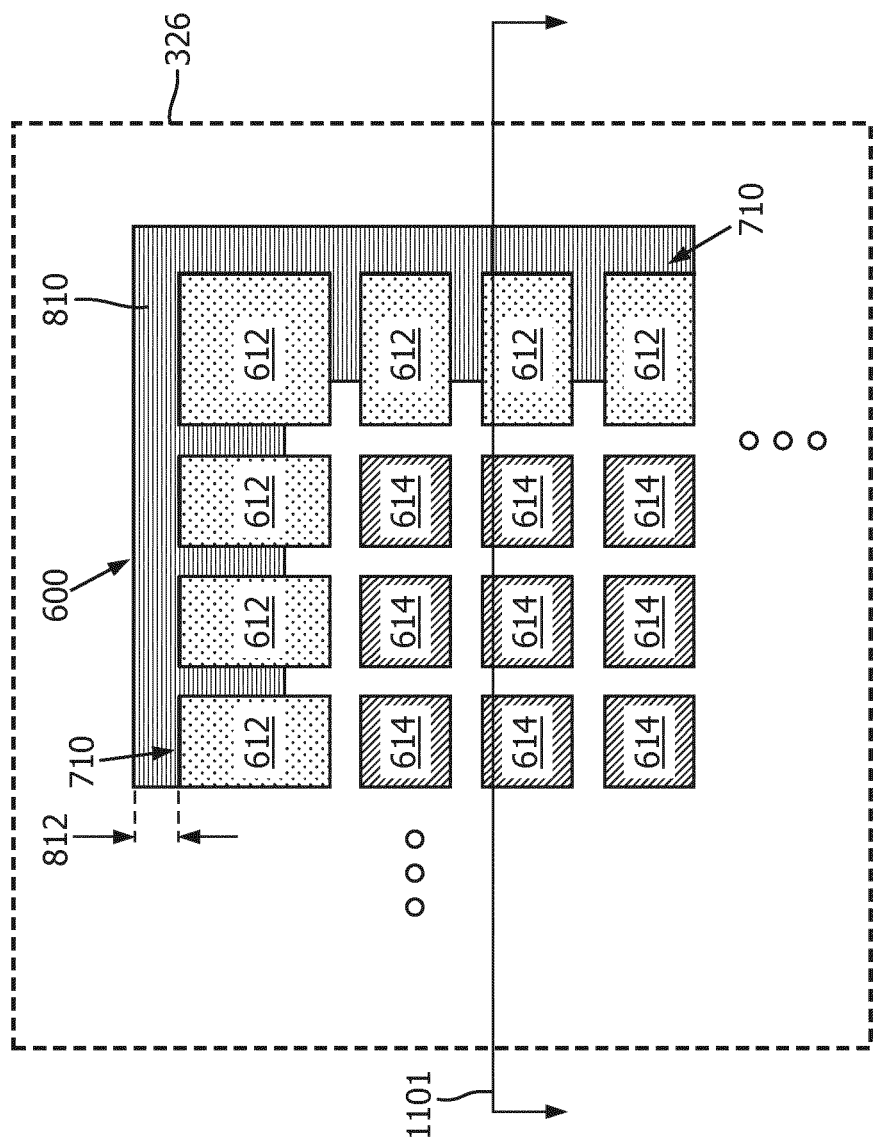
FIG. 11 is a top view of an array structure after excess sealing material is removed in a stage of manufacturing according to embodiments of the present disclosure.
Figure 12:
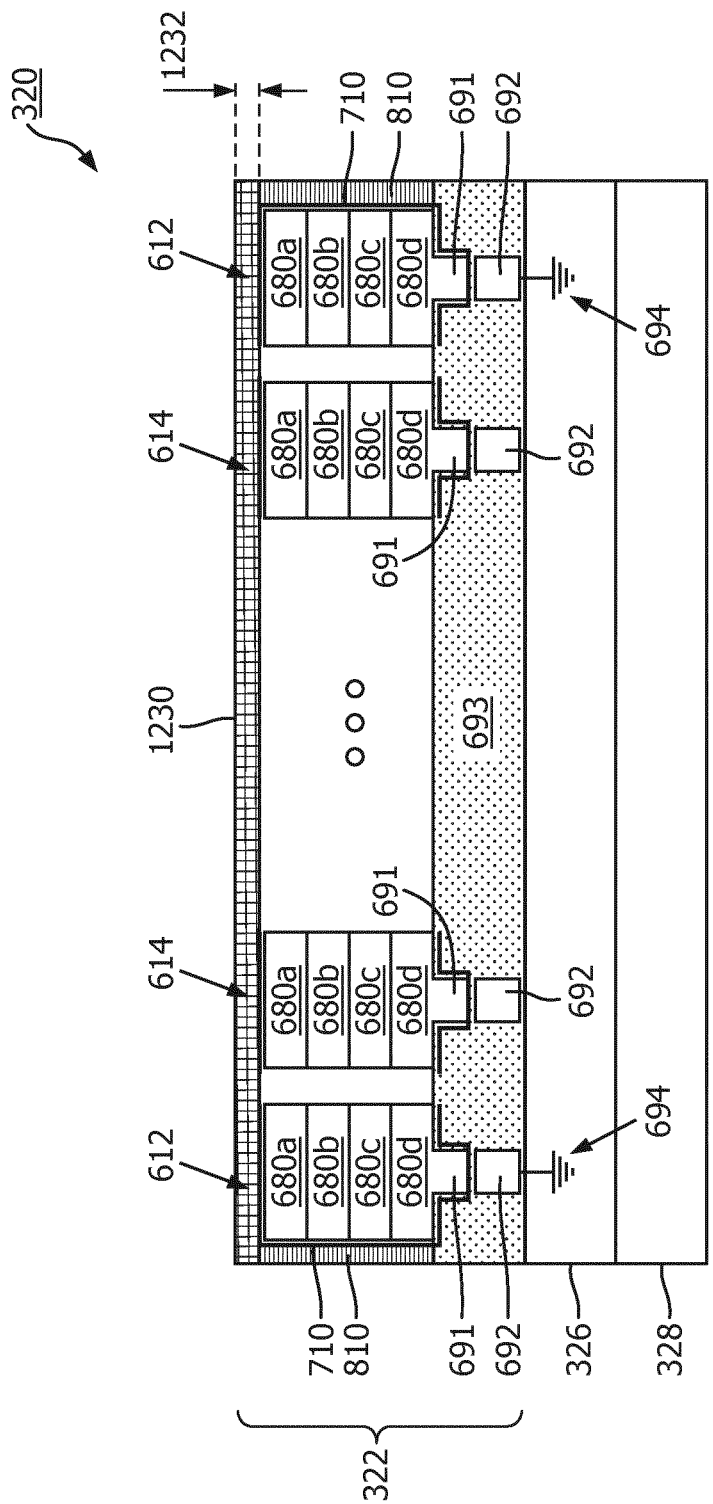
FIG. 12 is a cross-sectional view of an imaging component including an array structure in a stage of manufacturing according to embodiments of the present disclosure.

A method 500 of manufacturing an imaging component 320 is described with reference made to FIGS. 5-13. FIG. 5 is a flow diagram of a method 500 of manufacturing the imaging component 320 according to embodiments of the present disclosure. It is understood that additional steps can be provided before, during, and after the steps of method 500, and some of the steps described can be replaced or eliminated for other embodiments of the method. The steps of the method 500 can be carried out by a manufacturer of a catheter. FIG. 6 is a top view of an array structure 600 coupled to the IC layer 326 in a stage of manufacturing according to embodiments of the present disclosure. FIG. 7 is a cross-sectional view of the array structure 600 coupled to the IC layer 326 in a stage of manufacturing according to embodiments of the present disclosure. FIG. 8 is a top view of the array structure 600 sealed with a sealing material 810 in a stage of manufacturing according to embodiments of the present disclosure. FIG. 9 is a top view of the array structure 600 under a wicking process in a stage of manufacturing according to embodiments of the present disclosure. FIG. 10 is a top view of the array structure 600 after the wicking process is completed in a stage of manufacturing according to embodiments of the present disclosure. FIG. 11 is a top view of the array structure 600 after excess sealing material is removed in a stage of manufacturing according to embodiments of the present disclosure. FIG. 12 is a cross-sectional view of the imaging component 320 including the array structure 600 in a stage of manufacturing according to embodiments of the present disclosure.

Referring to the step 510 of the method 500 and FIGS. 6 and 7, in an embodiment, an array of ultrasound transducer elements 614 separated by air kerfs 618 is formed, for example, using a machining or dicing process or any suitable process. The ultrasound transducer elements 614 correspond to the ultrasound transducer elements 324. The ultrasound transducer elements 614 form part of an array structure 600 shown in in FIGS. 6 and 7.

Referring to the step 520 of the method 500 and FIGS. 6 and 7, in an embodiment, a plurality of buffer elements 612 surrounding the array of ultrasound transducer elements 614 are formed. The plurality of buffer elements 612 is separated by gaps 616. The buffer elements 612 do not include transducer functionalities. The buffer elements 612 do not emit ultrasound energy when activated. The buffer elements 612 can provide array uniformity and function as a buffer to protect the ultrasound transducer elements 614, as described in greater detail herein. The buffer elements 612 form part of the array structure 600.

FIG. 6 illustrates a top view of the array structure 600 bonded to a top plane 650 of the IC layer 326. The array structure 600 can be uniformly shaped and can have a rectangular shape or a square shape. As shown, the ultrasound transducer elements 614 are arranged in rows and columns. The buffer elements 612 are positioned on the outer-most rows and outer-most columns of the array structure 600 surrounding the ultrasound transducer elements 614. The buffer elements 612 define the sides of the array structure 600. The buffer elements 612 are separated from the ultrasound transducer elements 614 by air kerfs 620. In some embodiments, the ultrasound transducer elements 614 and the buffer elements 612 can be uniformly spaced. Thus, the air kerfs 618 and 620 and the gaps 616 can have substantially similar widths and can be aligned to each other.

Dimensions of the array structure 600 may vary in different embodiments. In some embodiments, the ultrasound transducer elements 614 can have lengths 602 between about 90 μm to about 130 μm and widths 604 between about 90 μm to about 130 μm. The widths 622 of the air kerfs 618, the widths 624 of the gaps 616, and the widths 626 of the air kerfs 620 can be between about 18 μm to about 30 μm. The buffer elements 612 can be sized to provide a buffering region with at least a depth 628 of about 100 μm for the array structure 600.

FIG. 7 illustrates a cross-sectional view of the array structure 600 coupled to the IC layer 326 taken along the line 601 of FIG. 6. The ultrasound transducer elements 614 and the buffer elements 612 include a matching layer 680a, a piezoelectric layer 680b, a dematching layer 680c, and a bump layer 680d. The matching layer 680a matches the acoustic impedance of the piezoelectric layer 680b to that of the body being diagnosed. The piezoelectric layer 680b transmits ultrasound waves and receives echoes reflected off target tissue structures. The dematching layer 680c reflects backward ultrasound waves travelling from the backside of the piezoelectric layer 680b. The bump layer 680d includes flip-chip bumps 691. The matching layer 680a, the dematching layer 680c, and the bump layer 680d can be composed of suitable conductive materials. The piezoelectric layer 680b can be composed of lead zirconium titanate (PZT). The IC layer 326 includes bump pads 692 coupled to the flip-chip bumps 691. An underfill material 693 fills the region between the bump layer 680d and the IC layer 326. The outer edges of the array structure 600 can be plated with a metalized ground edge plating 710, which may be composed of any suitable conductive material (e.g., gold).

Referring to the step 530 of the method 500 and FIGS. 8 and 9, in an embodiment, at least a portion of the gaps 616 between the plurality of buffer elements 612 are filled with a sealing material 810. The ground edge plating 710 on top of the array structure 600 is not shown in FIG. 8 for clarity of illustration. For example, the sealing material 810 is applied around sides 630 of the array structure 600 and wicked into the gaps 616 between the plurality of buffer elements 612. The sealing material 810 can be a curable ultraviolet (UV) epoxy material or any suitable material. FIG. 8 shows the array structure 600 with the sealing material 810 surrounding the sides 630. FIG. 9 shows the sealing material 810 wicking or spreading into the gaps 616. The spreading is shown by the arrows in FIG. 9. The sealing material 810 is allowed to wick into a pre-determined portion of the gaps 616 (e.g., before reaching the air kerfs 618 and 620) as shown by the dotted lines 901. The pre-determined portion can vary in different embodiments. In some embodiments, the pre-determined portion includes a depth 920 of at least 20 μm from an outer-boundary of the buffer elements 612. In some embodiments, the sealing material 810 can be cured by applying a UV activating light to the sealing material before the sealing material reaches the air kerfs 618, 620. In other embodiments, the sealing material 810 can be cured by any suitable process, such as by applying heat, chemicals, and/or wavelengths of light other than ultraviolet light (e.g., visible light, infrared light, etc.).

Referring to the step 540 of the method 500 and FIG. 10, in an embodiment, the sealing material 810 filling the gaps 616 between the plurality of buffer elements 612 is cured such that the array of ultrasound transducer elements 614 remain spaced apart by the air kerfs 618 and 620. FIG. 10 shows that the sealing material 810 is spread into the gaps 616 reaching the pre-determined portion. The curing can include applying a UV light to stop the spreading or wicking of the sealing material 810 when the pre-determined portion is filled.

Referring to the step 550 of the method 500 and FIGS. 10 and 11, in an embodiment, excess sealing material 810 is removed, for example, by dicing along the dashed lines 1010 in FIG. 10. FIG. 11 shows the array structure 600 after the excess sealing material 810 is removed. In some embodiments, the remaining sealing material 810 can have a thickness 812 between about 20 μm to about 40 μm.

Referring to the step 560 of the method 500 and FIG. 12, in an embodiment, a ground plane 1230 is bonded to the top of the array structure 600 to form the imaging component 320. FIG. 12 illustrates a cross-sectional view of the imaging component 320 including the array structure 600 taken along the line 1101 of FIG. 11. The ground plane 1230 can be a polyester film with gold metallization. Dimensions of the ground plane 1230 may vary in different embodiments. In some embodiments, the ground plane 1230 can have a thickness 1232 of about 5 μm. The ground plane 1230 provides an electrical ground return for the array structure 600. For example, the outer-most bump pads 692 are connected to ground connections 694 as shown in FIG. 12.

After forming the imaging component 320, the imaging component 320 can be positioned in the tip member 310 as shown in FIG. 3. The tip member 310 can be filled with an encapsulating material to secure the imaging component 320 within the tip member 310. The encapsulating material may include polydimethylsiloxane (PDMS), polyurethane, UV adhesives, or any suitable material that have desirable characteristics such as acoustic properties, bonding strength, and ease to work with during manufacturing.

The use of the sealing material 810 around the array structure 600 and partially filling the gaps 616 between the buffer elements 612 prevent the encapsulating material from wicking into the air kerfs 618 between the ultrasound transducer elements 614. As described above, the sealing material 810 can have a thickness 812 between about 20 μm to about 40 μm. Thus, the disclosed embodiments can create air-filled kerfs with a minimal increase in the size of the imaging component. For example, the disclosed embodiments can be applied to fabricate an imaging component for intraluminal imaging, where the intraluminal device probe (e.g., the tip assembly 102) carrying the imaging component can be directed between ribs of the human body. In addition, the disclosed fabrication method is suitable for bulk production and automation.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An imaging assembly for an intraluminal device, comprising:

a plurality of ultrasound transducer elements spaced apart by air kerfs;

a plurality of buffer elements surrounding the plurality of ultrasound transducer elements, wherein the plurality of buffer elements do not emit ultrasound energy, and wherein the plurality of buffer elements are spaced apart by gaps; and a sealing material filling a first portion of each of the gaps between the plurality of buffer elements, wherein the sealing material does not fill a second portion of each of the gaps between the plurality of buffer elements, and wherein the sealing material does not fill the air kerfs.

2. The imaging assembly of claim 1, wherein the air kerfs separate adjacent ultrasound transducer elements by a distance of 30 micrometers or less.

3. The imaging assembly of claim 2, wherein the gaps between the plurality of buffer elements are aligned to the air kerfs.

4. The imaging assembly of claim 3, wherein the sealing material fills the portions of the gaps to a depth of at least 20 micrometers from an outer boundary of the plurality of buffer elements.

5. The imaging assembly of claim 1, wherein the sealing material includes an ultraviolet epoxy material.

6. The imaging assembly of claim 1, further comprising:

a ground edge plating to provide a ground return for the plurality of ultrasound transducer elements; and a ground plane connecting the plurality of ultrasound transducer elements and the plurality of buffer elements to the ground edge plating.

7. The imaging assembly of claim 1, further comprising:

an integrated circuit (IC) layer, wherein the plurality of ultrasound transducer elements is positioned adjacent a top plane of the IC layer; and a backing layer positioned adjacent a bottom plane of the IC layer.

8. The imaging assembly of claim 1, further comprising an encapsulating material securing the imaging assembly within the intraluminal device, wherein the sealing material prevents the encapsulating material from reaching the air kerfs.

* * * * *